United States Patent [19]

Mickel

[11] Patent Number: 5,500,418
[45] Date of Patent: Mar. 19, 1996

[54] AMINOALKANEPHOSPHINIC ACIDS AND SALTS THEREOF

[75] Inventor: Stuart J. Mickel, Lausen, Switzerland

[73] Assignee: Ciba-Geigy Corporation, Tarrytown, N.Y.

[21] Appl. No.: 308,040

[22] Filed: Sep. 16, 1994

Related U.S. Application Data

[62] Division of Ser. No. 979,513, Nov. 19, 1992, Pat. No. 5,376,684.

[30] Foreign Application Priority Data

Nov. 21, 1991 [CH] Switzerland .................... 3404/91

[51] Int. Cl.$^6$ .................... A61K 31/665; C07F 9/30; C07D 221/00
[52] U.S. Cl. .................... 514/100; 514/82; 514/89; 514/553; 549/220; 546/22; 546/23
[58] Field of Search .................... 546/22, 23; 549/221, 549/220; 514/99, 79, 82, 553, 89, 100

[56] References Cited

U.S. PATENT DOCUMENTS

| | | | |
|---|---|---|---|
| 4,536,355 | 8/1985 | Lee et al. | 71/87 |
| 4,618,358 | 10/1986 | Maier | 71/86 |
| 4,656,298 | 4/1987 | Dingwall et al. | 556/12 |
| 4,772,738 | 9/1988 | Dingwall et al. | 558/175 |
| 4,908,465 | 3/1990 | Dingwall et al. | 558/175 |
| 5,004,826 | 4/1991 | Dingwall et al. | 558/169 |
| 5,013,863 | 5/1991 | Baylis et al. | 562/11 |
| 5,039,685 | 8/1991 | Knutsen et al. | 514/326 |
| 5,051,524 | 9/1991 | Baylis et al. | 558/145 |
| 5,064,819 | 11/1991 | Baylis et al. | 514/114 |
| 5,071,859 | 12/1991 | Knudsen et al. | 514/326 |
| 5,190,933 | 3/1993 | Baylis et al. | 514/114 |
| 5,190,934 | 3/1993 | Mickel et al. | 514/114 |
| 5,229,379 | 7/1993 | Marescaux et al. | 514/114 |
| 5,243,062 | 9/1993 | Dingwall et al. | 558/169 |
| 5,281,747 | 1/1994 | Hall et al. | 562/11 |
| 5,300,679 | 4/1994 | Baylis et al. | 562/11 |
| 5,332,729 | 7/1994 | Mickel et al. | 514/114 |
| 5,376,684 | 12/1994 | Mickel | 514/553 |
| 5,407,922 | 4/1995 | Marescaux et al. | 514/89 |
| 5,424,441 | 6/1995 | Mickel et al. | 548/131 |

FOREIGN PATENT DOCUMENTS

| | | |
|---|---|---|
| 2045077 | 12/1991 | Canada. |
| 0181833 | 5/1986 | European Pat. Off.. |
| 0319482 | 6/1989 | European Pat. Off.. |
| 0356128 | 2/1990 | European Pat. Off.. |
| 0399949 | 11/1990 | European Pat. Off.. |
| 0402312 | 12/1990 | European Pat. Off.. |
| 904203 | 2/1991 | South Africa. |
| 914791 | 3/1992 | South Africa. |
| 1525262 | 9/1978 | United Kingdom. |

OTHER PUBLICATIONS

J. Neural Transm (1992) [Suppl] 35: 37–69 Marescaux et al, Genetic absence epilepsy in rats from Strasbourg—A review.

Hosford et al "Anatomic Distribution of the Immediate—Early Gene C–Fos in Amygdala Kingling" Annual Meeting of the American Academy of Neurology Boston Mass. Apr. 20–27 (1991) Neurology 41—(Suppl) p. 151 Abstract No. 1 130 S. Mar. 1991.

J. G. Dingwall "New Carboxyphosphonic and phosphinic Acid Structures of Technical and Biological Interest" Phosphorous and Sulfur v. 18. (353–6) 1983.

Walter et al "Herbicidal Methylphosphinic Acid Derivatives" Chem. Abs. vol. 97: 72585v (1982).

Hosford et al "The Lethargic Mouse. A genetic Model of Absence Epilepsy" 21st Annual Meeting New Orleans Louisiana. Nov. 10–15 1991 Society for Neuroscience—Abstract p. 170 vol. 17—(1991).

Neuroscience Letters. 33 (1982) 97–101 Vergnes et al Spontaneous Paroxysmal Electroclinical Patterns in Ral: A Model of Generalized Non–Convulsive Epilepsy.

*Primary Examiner*—C. Warren Ivy
*Assistant Examiner*—Amelia Owens
*Attorney, Agent, or Firm*—Irving M. Fishman; Karen Kaiser

[57] ABSTRACT

Compounds of formula I $$\begin{array}{c} HO\diagdown\overset{O}{\underset{\|}{P}}-CH_2-\overset{R_1}{\underset{|}{CH}}-CH_2-N\diagup\overset{R_2}{\diagdown R_3} \\ R\diagup \end{array} \quad (I)$$

wherein R is diethoxymethyl, $R_1$ is hydrogen, $R_2$ is pyrid-3-ylmethyl and $R_3$ is hydrogen, or R is cyclohexylmethyl, $R_1$ is hydrogen and $R_2$ is quinolin-4-ylmethyl, or $R_1$ is hydroxy and $R_2$ is 3,4-methylenedioxybenzyl, 1-(3,4-methylenedioxyphenyl)ethyl, and $R_3$ is hydrogen, or R is benzyl, $R_1$ is hydroxy, $R_2$ is 1-(3,4-methylenedioxyphenyl)ethyl, and $R_3$ is hydrogen, and salts thereof have $GABA_B$-antagonistic properties and can be used for the treatment of diseases responsive to $GABA_B$-antagonists.

9 Claims, No Drawings

AMINOALKANEPHOSPHINIC ACIDS AND SALTS THEREOF

This is a DIVISIONAL of Ser. No. 979,513, filed Nov. 19, 1992 now U.S. Pat. No. 5,376,684.

The invention relates to compounds of formula I

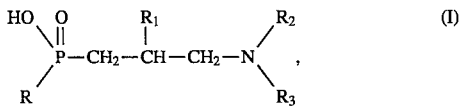

wherein a) R is butyl, $R_1$ is hydrogen, $R_2$ is 3,4-dichlorobenzyl, 1-(4-chlorophenyl)ethyl or 1-(3,4-dichlorophenyl)ethyl and $R_3$ is hydrogen, or b) R is diethoxymethyl, $R_1$ is hydrogen and $R_2$ is 2,6- or 3,5-dichlorobenzyl, pyrid-3-ylmethyl, 1-(4-methoxyphenyl)ethyl, 1-(4-chloro-3-iodo-phenyl)ethyl or 1-(3-chloro-4-iodo-phenyl)ethyl, or R1 is hydroxy and $R_2$ is 3,4-dichlorobenzyl, 1-(3-chloro-4-iodo-phenyl)ethyl, 1-(4-chloro-3-iodo-phenyl)ethyl or 1-(3,4-dichlorophenyl)ethyl and $R_3$ is hydrogen, or c) R is cyclohexylmethyl, $R_1$ is hydrogen and $R_2$ is 3,5-dichlorobenzyl, quinolin-4-ylmethyl, 1-(3-chlorophenyl)ethyl or 1-(3,4,5-trimethoxyphenyl)ethyl, or $R_1$ is hydroxy and $R_2$ is 3,4-dimethylbenzyl, 3,4-methylenedioxybenzyl, 1-(3-chlorophenyl)ethyl, 1-(3,4-dichlorophenyl)ethyl, 1-(3-chloro-4-iodo-phenyl)ethyl, 1-(4-chloro-3-iodo-phenyl)ethyl, 1-(2,4-dimethoxyphenyl)ethyl, 1-(2,5-dimethoxyphenyl)ethyl, 1-(2,6-dimethoxyphenyl)ethyl, 1-(3,4-dimethoxyphenyl)ethyl, 1-(3,4-methylenedioxyphenyl)ethyl, 1-(3,5-dimethoxyphenyl)ethyl, 1-(3,4,5-trimethoxyphenyl)ethyl, 3-phenylprop-2-yl, 2-(3,4-dichlorophenyl)propyl, 2-(3,4-dichlorophenyl)propyl, 3-(3,4-dichlorophenyl)prop-2-yl or 3-phenyl-3-hydroxy-prop-2-yl and $R_3$ is hydrogen, or R is cyclohexylmethyl, $R_1$ is hydrogen, $R_2$ is 4-chlorobenzyl and $R_3$ is methyl, or d) R is cyclohex-3-enylmethyl, $R_2$ is (S)-hydroxy, $R_2$ is 1(S)-(3,4-dichlorophenyl)ethyl and $R_3$ is hydrogen, or e) R is benzyl, $R_1$ is hydroxy, $R_2$ is α-cyclopropyl-3,4-dichloro-benzyl, 3,4,5-trimethoxybenzyl, 1-(3,5-dimethoxyphenyl)ethyl, 1-(3,4-dichlorophenyl)ethyl, 2-(3,4-dichlorophenyl)ethyl, 1-(3-chloro-4-iodo-phenyl)ethyl, 1-(3,4-dichlorophenyl)-2-hydroxy-ethyl, 2-(3,4-dichlorophenyl)-2-hydroxy-ethyl, 1-(2,4-dimethoxyphenyl)ethyl, 1-(2,5-dimethoxyphenyl)ethyl, 1-(2,6-dimethoxyphenyl)ethyl, 1-(3,4-dimethoxyphenyl)ethyl, 1-(3,4-methylenedioxyphenyl)ethyl, 1-(3,4,5-trimethoxyphenyl)ethyl, 3-phenylprop-2-yl, 3-phenyl-3-hydroxy-prop-2-yl, 1-, 2- or 3-(3,4-dichlorophenyl)propyl, 3-(3,4-dichlorophenyl)prop-2-yl, 3-(3,4-dichlorophenyl)-3-hydroxy-prop-2-yl or 4-(3,4-dichlorophenyl)butyl and $R_3$ is hydrogen, or R is 4-chlorobenzyl, 4-methylbenzyl, 4-methoxybenzyl or cyclohex-3-enylmethyl and $R_1$, $R_2$ and $R_3$ are hydrogen, and salts thereof, to processes for the preparation of the compounds according to the invention, to pharmaceutical compositions comprising them and to the use thereof as active ingredients in medicaments.

As a result of their amphoteric nature, the compounds of formula I are in the form of internal salts and may form both acid addition salts and salts with bases.

Acid addition salts of compounds of formula I are, for example, pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexylsulfamates (cyclamates).

Salts of compounds of formula I with bases are, for example, salts thereof with pharmaceutically acceptable bases, such as non-toxic metal salts derived from metals of groups Ia, Ib, IIa and IIb, for example alkali metal salts, especially sodium or potassium salts, alkaline earth metal salts, especially calcium or magnesium salts, and also ammonium salts with ammonia or organic amines or quaternary ammonium bases, such as unsubstituted or C-hydroxylated aliphatic amines, especially mono-, di- or tri-lower alkylamines, for example methyl-, ethyl- or diethyl-amine, mono-, di- or tri-(hydroxy-lower alkyl)amines, such as ethanol-, diethanol- or triethanol-amine, tris(hydroxymethyl)methylamine or 2-hydroxy-tert-butylamine, or N-(hydroxy-lower alkyl)-N,N-di-lower alkylamines or N-(polyhydroxy-lower alkyl)-lower alkylamines, such as 2-(dimethylamino)ethanol or D-glucamine, or quaternary aliphatic ammonium hydroxides, for example tetrabutylammonium hydroxide.

Depending upon the presence of asymmetric carbon atoms, the compounds according to the invention may be in the form of mixtures of isomers, especially in the form of racemates, or in the form of pure isomers, especially in the form of optical antipodes.

The novel compound of formula I and the pharmaceutically acceptable salts thereof also exhibit valuable $GABA_B$-antagonistic properties. In particular, they exhibit effective bonding to the $GABA_B$-receptor and prove to be antagonists of GABA (γ-aminobutyric acid) at that receptor. Seen mechanistically, antagonism at $GABA_B$-receptors can increase the release of rapid stimulus amino acid transmitters, that is to say glutamic acid and aspartic acid, and thus improve information processing in the brain. This is consistent with the finding that the late post-synaptic inhibition potential in the hippocampus, which is ascribed to a $GABA_B$-mechanism, is reduced by the antagonists and therefore allows a more rapid nerve impulse transmission sequence.

On the other hand, it has been found that in rats chronic treatment with antidepressants and repeated electric shocks increase the number of $GABA_B$-receptors in the cerebral cortex. In accordance with receptor theories, chronic treatment with $GABA_B$-antagonists should result in the same effect. For this and other reasons, $GABA_B$-antagonists may therefore act as antidepressants.

The novel $GABA_B$-antagonists according to the invention interact at the $GABA_B$-receptor with $IC_{50}$ values of approximately $10^{-8}$M (mol/l) and above in the corticocerebral membranes of rats. Unlike $GABA_B$-agonists such as baclofen, they do not potentiate the stimulation of adenylate cyclase in rat cerebral cortex sections by noradrenaline, but act as an antagonist of baclofen action. The antagonism towards baclofen can also be shown in vitro in electrophysiological models, for example in the penicillin-induced "epileptic" hippocampus section preparation in which baclofen in a concentration of 6 μM (micromol/liter) inhibits "epilepsy-like" discharges from pyramidal cells. The compounds according to the invention act as antagonists of baclofen action in concentrations of about 10 to about 100

μM (micromol/liter). In vivo the antagonism can be shown by iontophoresis of baclofen in rat cerebral cortex and by systemic use of antagonists in doses of from 10 to 100 mg/kg. In doses of about 30 mg/kg, antagonism occurs towards the muscle-relaxant action of baclofen, which is measured in the Rotarod model.

The novel $GABA_B$-antagonists not only exhibit antagonism towards baclofen but also have an independent action as antagonists of endogenous GABA. Accordingly, the antagonists are active in conventional behaviour models that are characteristic of antidepressive, anxiolytic and/or nootropic states. For example, it has been found that, on oral administration, compounds of formula (I) are active in the floating test in accordance with Porsolt, in the Geller test, the delayed passive avoidance test (single test modification) in pre-test and post-test situations, in the two-chamber test and in the complex labyrinth. In addition, in tests on Rhesus monkeys, an increase in play instinct, curiosity and social grooming behaviour and a reduction in anxiety symptoms were observed.

The novel compounds of formula I and their pharmaceutically acceptable salts are therefore excellently suitable as nootropics, antidepressants and anxiolytics, for example for the treatment of the symptoms of cerebral insufficiency, depressive moods and anxiety states.

On the basis of the antagonism of the $GABA_B$-antagonists of baclofen already known, it has hitherto been assumed that $GABA_B$-antagonists, such as compounds of formula I, have no anti-epileptic activity component.

Surprisingly it has now been found that $GABA_B$-antagonists, especially compounds of formula I, exhibit in vivo marked anti-absence properties.

Those properties can be documented in a certain strain of rats on the basis of their marked inhibitory action on spontaneous "spike and wave" discharges in the following animal model for absence epilepsy.

Approximately 30% of the Wistar rats bred in the Centre de Neurochimie in Strasbourg exhibit spontaneous behaviour alterations amongst which electro-encephalogram (EEG) and symptoms are comparable to human absences (petit mal). Synchronous "spike and wave" discharges (SWD; frontoparietal-cortex; 7–8 Hz; 300–1000 μV, duration 0.5 to 40 sec, mean value=6.0±3:3.4 sec) and more frequently *Myoclonia facialis* accompany a cessation of behaviour. These absence-like conditions occur spontaneously and repeatedly. By selectively breeding those rats it has been possible to obtain a strain in which 100% of the rats exhibit those SWD (epileptic rats). Conversely, it has been possible to breed a strain in which 100% of the rats are free of SWD (control rats). This pharmacological model is described in Vergnes M., Marescaux C., Micheletti G., Reis J., Depaulis A., Rumbach L. and Warter J. M., Neurosci. Lett. 33, 97–101 (1982).

In this model, for example, the clinically used anti-epileptics ethosuximide, diazepam, trimethadione and sodium valproate in doses $\geq 25$ mg/kg (ethosuximide), $\geq 0.5$ mg/kg (diazepam) and $\geq 50$ mg/kg (trimethadione and sodium valproate) reduce the spike and wave discharges in dependence upon dosage. Carbamazepine and phenytoin are ineffective or worsen the attacks at higher doses. Phenobarbitone is effective at 2.5 to 10 mg/kg and is ineffective at 20 mg/kg. The action of those anti-epileptics on crises in rats and absences in human beings supports the hypothesis that this animal model represents a pharmacological model for absence epilepsy. Its predictive value appears to be at least as good as that of other conventional animal models.

In addition to their suitability as nootropics, antidepressants and anxiolytics, the compounds of formula I and their pharmaceutically acceptable salts are therefore also excellently suitable as active ingredients in anti-epileptic medicaments for the treatment of epilepsy of the "petit mal" type, both of spontaneous absence epilepsy, such as spontaneous absence epilepsy in children and adolescents, and of atypical absences, such as absences of the Lennox-Gastaut syndrome, as well as those which occur as undesirable side-effects of treatment with customary "grand mal" anti-epileptics, such as phenytoin, carbamazepine or Vigabatrin®, and anti-epileptics having the same or a similar activity profile.

The invention relates, for example, to compounds of formula I wherein a) R is butyl, $R_1$ is hydrogen, $R_2$ is 3,4-dichlorobenzyl, 1-(4-chlorophenyl)ethyl or 1-(3,4-dichlorophenyl)ethyl and $R_3$ is hydrogen, or b) R is diethoxymethyl, $R_1$ is hydrogen and $R_2$ is 2,6- or 3,5-dichlorobenzyl, pyrid-3-ylmethyl or 1-(4-methoxy)phenethyl, or $R_1$ is hydroxy and $R_2$ is 3,4-dichlorobenzyl, 1-(3-chloro-4-iodo-phenyl)ethyl or 1-(4-chloro-3-iodo-phenyl)ethyl and $R_3$ is hydrogen, or c) R is cyclohexylmethyl, $R_1$ is hydrogen and $R_2$ is 3,5-dichlorobenzyl, 1-(3-chlorophenyl)ethyl or quinolin-4-ylmethyl, or $R_1$ is hydroxy and $R_2$ is 3,4-dimethylbenzyl or 1-(3-chlorophenyl)ethyl, 1-(3,4-dichlorophenyl)ethyl, 1-(3-chloro-4-iodo-phenyl)ethyl, 1-(4-chloro-3-iodo-phenyl)ethyl, 1-(3,5-dimethoxyphenyl)ethyl, 1-(3,4,5-trimethoxyphenyl)ethyl, 3-phenylprop-2-yl, 3-(3,4-dichlorophenyl)prop-2-yl or 3-phenyl-3-hydroxy-prop-2-yl and $R_3$ is hydrogen, or $R_1$ is hydrogen, $R_2$ is 4-chlorobenzyl and $R_3$ is methyl, or d) R is cyclohex-3-enylmethyl, $R_1$ is hydroxy and $R_2$ is 1-(3,4-dichlorophenyl)ethyl and $R_3$ is hydrogen, or e) R is benzyl, $R_1$ is hydroxy, $R_2$ is 3,4,5-trimethoxybenzyl, 1-(3,5-dimethoxyphenyl)ethyl, 1-(3,4-dichlorophenyl)ethyl, 2-(3,4-dichlorophenyl)ethyl, 1-(3-chloro-4-iodo-phenyl)ethyl, 1-(3,4-dichlorophenyl)-2-hydroxy-ethyl, 2-(3,4-dichlorophenyl)-2-hydroxy-ethyl, 1-, 2- or 3-(3,4-dichlorophenyl)propyl, 3-phenylprop-2-yl, 3-phenyl-3-hydroxy-prop-2-yl, 3-(3,4-dichlorophenyl)prop-2-yl, 3-(3,4-dichlorophenyl) -3-hydroxy-prop-2-yl or 4-(3,4-dichlorophenyl)butyl und $R_3$ is hydrogen, and salts thereof, especially pharmaceutically acceptable salts thereof.

The invention relates especially to compounds of formula I wherein

R is cyclohexylmethyl or benzyl, $R_1$ is hydroxy, $R_2$ is 1-(2,4-dimethoxyphenyl)ethyl, 1-(2,5-dimethoxyphenyl)ethyl, 1-(2,6-dimethoxyphenyl)ethyl, 1-(3,4-dimethoxyphenyl)ethyl, 1-(3,4-methylenedioxyphenyl)ethyl, 1-(3,5-dimethoxy-phenyl)ethyl or 1-(3,4,5-trimethoxyphenyl)ethyl and $R_3$ is hydrogen, and salts thereof, especially pharmaceutically acceptable salts thereof.

The invention relates more especially to compounds of formula I wherein R is cyclohexylmethyl or benzyl, $R_1$ is hydroxy, $R_2$ is 1-(3,4,5-trimethoxyphenyl)ethyl and $R_3$ is hydrogen, and salts thereof, especially pharmaceutically acceptable salts thereof.

The invention in each case preferably relates to those of the above-defined compounds wherein $R_1$ is hydroxy and the carbon atom carrying the hydroxy group and, where present, the α-carbon atom of 1-(3,4-dichloro-, 3-chloro-4-iodo-, 4-chloro-3-iodo-, 2,4-di-methoxy-, 2,5-dimethoxy-, 2,4-dimethoxy-, 3,4-dimethoxy-, 3,5-dimethoxy-, 3,4,5-trimethoxy- and 3,4-methylenedioxy-phenyl)ethyl, α-cyclopropyl-4,4-dichloro-benzyl and 1-(3,4-dichlorophenyl)propyl have the (S)-configuration, R, $R_2$ and $R_3$ being as defined in each case.

The process for the preparation of the novel aminoalkanephosphinic acids of formula I provided in accordance with the invention comprises: in a compound of formula II,

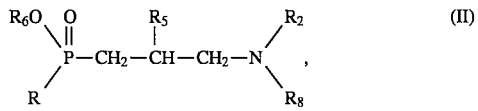

wherein $R_5$ is hydrogen or protected hydroxy, $R_6$ is a hydroxy-protecting group, $R_8$ is a group $R_3$ or an amino-protecting group and R and $R_2$ are as defined, or in a salt thereof, freeing the hydroxy groups by replacement of the hydroxy-protecting group $R_6$ by hydrogen and, where appropriate, removing the amino-protecting group $R_8$ and, where appropriate, freeing the hydroxy groups $R_1$ from the protected hydroxy group $R_5$ and, if desired, converting a resulting compound into a different compound of formula I, separating a mixture of isomers obtainable in accordance with the process into the components and isolating the preferred isomer and/or converting a free compound obtainable in accordance with the process into a salt or convening a salt obtainable in accordance with the process into the corresponding free compound.

The starting materials of formula II can be prepared by various methods, for example by a) in a compound of formula III

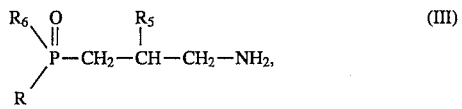

wherein R is as defined, $R_5$ is hydrogen or protected hydroxy and $R_6$ is a hydroxy-protecting group, introducing the group $R_2$ and, if desired, a radical $R_3$ other than hydrogen, or b) reacting a compound of formula IV

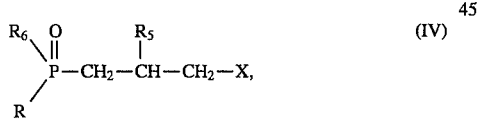

wherein R is as defined, $R_5$ is hydrogen or protected hydroxy, $R_6$ is a hydroxy-protecting group and X is a reactive esterified hydroxy group, or a salt thereof, with a compound of formula V

wherein $R_2$ is as defined and $R_8$ is a group $R_3$ or an amino-protecting group, or c) condensing a compound of formula VI

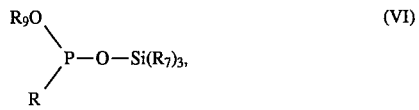

wherein $R_9$ is a hydroxy-protecting group $R_6$ or —Si($R_7$)$_3$ and R is as defined, the radicals $R_7$ being identical or different aliphatic hydrocarbon radicals, for example lower alkyl, especially methyl and/or tert-butyl, with a compound of formula VII

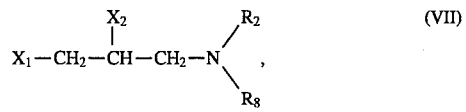

wherein $X_1$ is reactive esterified hydroxy and $X_2$ is hydrogen, or $X_1$ and $X_2$ together are epoxy and $R_8$ is a group $R_3$ or an amino-protecting group, or d) reacting a compound of formula VIII

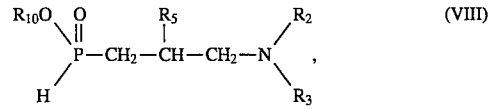

wherein $R_5$ is hydrogen or protected hydroxy, $R_{10}$ is hydrogen or a group $R_6$, and $R_2$ and $R_3$ are as defined, with a silylating agent, and reacting the resulting silyl-activated compound of formula VIII wherein $R_8$ is a group $R_3$ other than hydrogen or a group of the formula —Si($R_7$)$_3$, $R_{11}$ is a group $R_6$ or a group —Si($R_7$)$_3$, and $R_5$ is hydrogen or a group of the formula —OSi($R_7$)$_3$, the radicals $R_7$ being identical or different aliphatic hydrocarbon radicals, for example lower alkyl, especially methyl and/or ten-butyl, with a reactive ester of an aliphatic, cycloaliphatic, cycloaliphatic-aliphatic or araliphatic alcohol, with an aliphatic, cycloaliphatic, cycloaliphatic-aliphatic, araliphatic or heteroarylaliphatic hydrocarbon which may have an additional double bond in the α,β-position, with an aliphatic, cycloaliphatic, cycloaliphatic-aliphatic, araliphatic or heteroarylaliphatic aldehyde or ketone or with an aliphatic epoxide, or e) for the preparation of a compound of formula II wherein $R_2$ is hydroxy, reacting a compound of formula X

in the form of a metal salt of formula XI

wherein $R_{11}$ is a group $R_6$ or —Si($R_7$)$_3$ and R is as defined, wherein the radicals $R_7$ are identical or different aliphatic hydrocarbon radicals, for example lower alkyl, especially methyl and/or tert-butyl, and $M^+$ is an alkali, alkaline earth or transition metal cation, with an aldehyde of formula XII

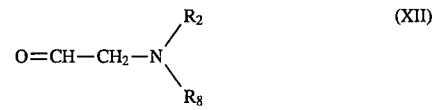

wherein $R_2$ is as defined and $R_8$ is a group $R_3$ or an amino-protecting group.

If desired, a radical $R_3$ other than hydrogen can be introduced into an initially obtained compound of formula II wherein $R_3$ is hydrogen.

The pharmaceutical compositions according to the invention are those in a unit dose form that comprise a therapeutically effective amount of active ingredient on its own or together with a pharmaceutically acceptable carrier, especially with inorganic or organic, solid or liquid, pharmaceutically acceptable carriers, so that they are suitable for enteral, such as oral and also rectal, and parenteral administration to warm-blooded animals.

The pharmaceutical compositions provided in accordance with the invention comprise, for example, from approximately 10% to approximately 80%, preferably from approximately 20% to approximately 60%, active ingredient. Pharmaceutical compositions according to the invention for enteral or parenteral administration are, for example, those in unit dose forms, such as dragées, tablets, capsules or suppositories, and also injection or infusion solutions, preferably in ampoules. These formulations are prepared in a manner known per se, for example by means of conventional mixing, granulating, confectioning, dissolving or lyophilising processes. For example, pharmaceutical compositions for oral use can be obtained by combining the active ingredient with solid carriers, optionally granulating a resulting mixture, and, if desired, processing the mixture or granules, if necessary with the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes, using, for example, corn, wheat, rice or potato starch, gelatin, tragacanth, methylcellulose and/or polyvinylpyrrolidone, and, if desired, disintegrators, such as the above-mentioned starches, also carboxymethyl starch, cross-linked polyvinylpyrrolidone, agar, alginic acid or a salt thereof, such as sodium alginate. Excipients are especially flow agents, flow conditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical compositions include dry-filled capsules consisting of gelatin, and also soft, sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycol, to which stabilisers may likewise be added.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycol or higher alkanols. It is also possible to use gelatin rectal capsules that comprise a combination of the active ingredient and a suppository base. Suitable suppository bases are, for example, liquid triglycerides, polyethylene glycols or paraffin hydrocarbons.

For parenteral administration there are especially suitable aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that comprise viscosity-increasing substances, for example sodium carboxymethylcellulose, sorbitol and/or dextran, and, if desired, stabilisers.

The pharmaceutical compositions may be sterilised and, if desired, may comprise further pharmacologically active ingredients and/or excipients, for example preservatives, stabilisers, wetting agents and/or emulsifiers, solubilisers, salts for regulating the osmotic pressure and/or buffers.

The dosage may depend upon various factors, such as mode of administration, species, age and/or individual condition. The daily dose to be administered in the case of oral administration is from approximately 5 to approximately 60 mg/kg, especially from 10 to approximately 40 mg/kg and, for warm-blooded animals having a body weight of about 40 kg, preferably from approximately 200 mg to approximately 2400 mg, especially from approximately 400 to approximately 1600 mg, which is advantageously divided into from 2 to 6, for example 3 or 4, individual doses.

The following Examples serve to illustrate the invention; temperatures are given in degrees Celsius and pressures in mbar.

EXAMPLE 1

A solution of 0.36 g of lithium hydroxide monohydrate in 7 ml of water is added to a solution of 1.61 g of 3-(3,5-dichlorobenzylamino)propyl(diethoxymethyl)-phosphinic acid ethyl ester in 3 ml of ethanol and heated at 60° for 24 hours. The mixture is then cooled to room temperature and the solvent is removed under reduced pressure. The evaporation residue is taken up in water and rendered neutral with phosphoric acid. A white precipitate is formed. The precipitate is filtered off and the filtrate is concentrated to dryness by evaporation. The white evaporation residue is dried under reduced pressure and crystallised from toluene/diethyl ether. Filtration with suction and drying yield 3-(3,5-dichlorobenzylamino)propyl(diethoxymethyl)phosphinic acid having a melting point of 160°–161°.

The starting material can be prepared, for example, as follows:

1.41 g of 3,5-dichlorobenzaldehyde are added to a solution of 2.53 g of 3-aminopropyl(diethoxymethyl)phosphinic acid ethyl ester in 10 ml of anhydrous methanol and the resulting clear solution is stirred at room temperature for 30 minutes. There are then added first 0.6 g of glacial acetic acid and then, dropwise, 0.21 g of sodium cyanoborohydride dissolved in 5 ml of methanol. An exothermic reaction begins. The reaction mixture is stirred for 3 hours at 20°, adjusted to pH 8, and the solvent is removed. The residue is dissolved in dichloromethane and washed with water. The organic phase is separated off, dried over sodium sulfate and concentrated to dryness by evaporation. The oil that remains behind is purified by chromatography on silica gel, yielding 3-(3,5-dichloro-benzylamino)propyl(diethoxymethyl)phosphinic acid ethyl ester in the form of a yellowish oil.

EXAMPLE 2

A solution of 4.1 g of 3-{N-[1-(3,4-dichlorophenyl)ethyl]amino}-2(S)-hydroxy-propyl(cyclohexylmethyl)phosphinic acid ethyl ester in 30 ml of 5N hydrochloric acid is heated at reflux for 24 hours, during which time two phases are formed. The reaction mixture is cooled to room temperature and the solvent is removed under reduced pressure; the residue is taken up in absolute ethanol and the residual water is distilled off azeotropically. The white solid that remains behind is crystallised from isopropanol, yielding 3-{N-[1-(3,4-dichlorophenyl)ethyl]amino}-2(S)-hydroxy-propyl(cyclohexylmethyl)phosphinic acid hydrochloride having a melting point of 174°–180°.

The starting material can be prepared as follows:

Under argon, a solution of 221 g of diethoxymethylphosphinic acid ethyl ester in 1000 ml of tetrahydrofuran is added dropwise in the course of 3 hours to a suspension of 26.4 g of 99% sodium hydride in 1500 ml of tetrahydrofuran, the temperature being maintained at 200°–25°. The reaction is exothermic and is associated with the evolution of gas. The mixture is stirred for 2 hours at room temperature and then 177.1 g of bromomethylcyclohexane are added in the course of 20 minutes; the mixture is stirred at reflux for 24 hours, then cooled to 0°, and 200 ml of water are carefully added. The solvent is removed under reduced pressure and the residue is partitioned between dichloromethane and water. The organic phase is separated off, dried over sodium sulfate and concentrated by evaporation under reduced pressure. The oil that remains behind is distilled under reduced pressure and yields diethoxymethyl(cyclohexylmethyl)phosphinic acid ethyl ester having a boiling point of 85° ($6 \times 10^{-4}$ bar).

107 g of trimethylchlorosilane are added to a solution of 151 g of diethoxymethyl(cyclohexylmethyl)phosphinic acid ethyl ester in 430 ml of dichloromethane that contains 10% by volume ethanol and the mixture is left to stand for 3 days at room temperature, then concentrated to dryness by evaporation and distilled under reduced pressure, yielding cyclohexylmethylphosphinic acid ethyl ester having a boiling point of 50° ($3 \times 10^{-4}$ bar).

20.0 g of cyclohexylmethylphosphinic acid ethyl ester are dissolved in 150 ml of tetrahydrofuran, and at 0° 11.0 g of triethylamine and then, dropwise, 12.0 g of trimethylchlorosilane are added, a white precipitate being formed. The resulting suspension is stirred at room temperature for 24 hours and then filtered under argon. The filtrate is concentrated by evaporation under reduced pressure. 10.9 g of (R)-epichlorohydrin and 2.0 g of anhydrous zinc chloride are added to the residue. When the exothermic reaction has died away, the mixture is heated under reflux at 60° for a further 24 hours. The reaction mixture is allowed to cool to room temperature, diluted with dichloromethane and washed with water. The organic phase is separated off, dried over sodium sulfate and concentrated by evaporation. The residue is dissolved in dichloromethane and washed with water. Drying over sodium sulfate and concentration by evaporation yield an oil. The oil is taken up in % methanolic acetic acid, left to stand at room temperature for 24 hours and then concentrated by evaporation. The residue is purified by chromatography on silica gel, yielding 3-chloro-2(R)-hydroxy-propyl(cyclohexylmethyl)phosphinic acid ethyl ester, $^1$H-NMR spectrum (in $CDCl_3$): δ=4.47 (1H, d), 4.21–4.02 (3H, m), 3.6 (2H, m), 2.11–1.54 (9H, m), 1.38–0.97 (9H, m).

A mixture of 4.24 g of 3-chloro-2(R)-hydroxy-propyl-(cyclohexylmethyl)-phosphinic acid ethyl ester, 2.85 g of 1-(3,4-dichlorophenyl)ethylamine, 1.95 g of Hünig base and 15 ml of ethanol is heated at reflux for 4 days. After cooling to room temperature and removal of the solvent under reduced pressure, the reaction mixture is partitioned between dichloro-methane and water, dried over sodium sulfate and again concentrated to dryness by evaporation. Chromatography on silica gel yields 3-{N-[1-(3,4-dichlorophenyl)ethyl]amino}-2(S)-hydroxy-propyl(cyclohexylmethyl)phosphinic acid ethyl ester, $[\alpha]_{20}^D = -1.8° \pm 0.9°$ (c=1.079 in chloroform).

EXAMPLE 3

In a manner analogous to that described in Example 1 it is possible to prepare 3-[N-(2,6-dichlorobenzyl)amino]propyl(diethoxymethyl)phosphinic acid, m.p. 171°–173°.

EXAMPLE 4

In a manner analogous to that described in Example 1 it is possible to prepare 3-[N-(pyrid-3-ylmethyl)amino]propyl(diethoxymethyl)phosphinic acid, m.p. 169°–171°.

EXAMPLE 5

In a manner analogous to that described in Example 1 it is possible to prepare 3-{N-[1-(4-methoxyphenyl)ethyl]amino}propyl-(diethoxymethyl)-phosphinic acid, m.p. 144°–146°.

EXAMPLE 6

A solution of 0.13 g of lithium hydroxide in 3 ml of water is added to a solution in 5 ml of ethanol of 1.1 g of 3-{N-1(S)-(3,4-dichlorophenyl)ethyl]amino}-2(S)-hydroxy-propyl-(cyclohex-3-enylmethyl)-phosphinic acid ethyl ester [obtainable as described in Example 2 starting from bromomethylcyclohex-3-ene and 1,1-diethoxyethylphosphinic acid ethyl ester via 3-chloro-2(R)-hydroxy-propyl-(cyclohex-3-enylmethyl)phosphinic acid ethyl ester and further reaction thereof with 1(S)-(3,4-dichlorophenyl)ethylamine] and the mixture is heated at 60° for 24 hours, then cooled to room temperature and concentrated by evaporation under reduced pressure. The residue is taken up in water, rendered neutral with aqueous phosphoric acid solution and again concentrated by evaporation under reduced pressure. The white solid that remains behind is taken up in hot methanol and filtered. Removal of the methanol yields a hygroscopic solid which, after crystallisation from cyclohexane/petroleum ether (60°–80°), yields 3-{N-[1(S)-(3,4-dichlorophenyl)ethyl]amino}-2(S)-hydroxy-propyl-(cyclohex-3-enylmethyl)-phosphinic acid in the form of a hygroscopic solid; $^1$H-NMR spectrum (in $CD_3OD$): δ=7.68 (1H), 7.58 (1H), 7.40 (1H), 6.60 (2H, CH=CH), 4.22 (1H, q, CH), 4.13 (1H, m), 2.97 (1H, dd), CHN), 2.63 (1H, dd, CHN), 2.33–1.21 (14H, m). The hydrochloride melts at 105°–206°.

EXAMPLE 7

In a manner analogous to that described in Example 2 it is possible to prepare 3-[N-(3,4,5-trimethoxybenzyl)amino]-2(S)-hydroxy-propyl-(benzyl)-phosphinic acid, m.p. 100°–102°.

EXAMPLE 8

In a manner analogous to that described in Example 2 it is possible to prepare 3-{N-[1-(3,4-dichlorophenyl)ethyl]amino}-2(S)-hydroxy-propyl-(benzyl)-phosphinic acid, m.p. 150°–158°;

3-[N-(3,4-dichloro-α-cyclopropyl-benzyl)amino]-2(S)-hydroxy-propyl-(benzyl)phosphinic acid, m.p. 204°–207°;

3-{N-[1(S)-(3,4-dichlorophenyl)ethyl]amino}-2(R)-hydroxy-propyl-(benzyl)-phosphinic acid, m.p. 188°–190°, and 3-{N-[1(R)-(3,4-dichlorophenyl)ethyl]amino} -2(S)-hydroxy-propyl-propyl-(benzyl)-phosphinic acid, $^1$H-NMR spectrum (in CD$_3$OD): δ=7.73 (1H, m, phenyl), 7.62 (1H, m, phenyl), 7.45 (1H, m, phenyl), 7.37–7.17 (5H, m, phenyl), 4.41 (1H, q, CHN), 4.21 (1H, q, CHN), 3.18 (2H, d, P—CH$_2$-phenyl), 3.05–2.88 (2H, m, CH$_2$N), 1.95 (2H, m, CH$_2$—P), 1.65 (3H, d, CH$_3$).

EXAMPLE 9

In a manner analogous to that described in Example 2 it is possible to prepare 3-[N-(3,4-dimethylbenzyl)amino]-2(S)-hydroxypropyl-(cyclohexylmethyl)-phosphinic acid, m.p. 164°–166°.

EXAMPLE 10

In a manner analogous to that described in Example 2 it is possible to prepare 3-{N-[1-(4-chloro-3-iodo-phenyl)ethyl] amino} -2(S)-hydroxy-propyl-(benzyl)-phosphinic acid hydrochloride, m.p. 118°–124°.

EXAMPLE 11

In a manner analogous to that described in Example 6 it is possible to prepare 3-{N-[1-(3,4,5-trimethoxyphenyl)ethyl]amino}-2(S)-hydroxy-propyl-cyclohexylmethyl-phosphinic acid hydrochloride, m.p. 175°–182°, and also 3-{N-[1(S)-(3,4,5-trimethoxyphenyl)ethyl]amino} -propyl-(cyclohexylmethyl)-phosphinic acid, m.p. 208°–209°.

EXAMPLE 12

In a manner analogous to that described in Example 6 it is possible to prepare

3-{N-[1-(3,5-dimethoxyphenyl)ethyl]amino}-2(S)-hydroxy-propyl-(benzyl)-phosphinic acid, m.p. 150°–165°;

3-{N-[1-(2,5-dimethoxyphenyl)ethyl]amino}-2(S)-hydroxy-propyl-(benzyl)-phosphinic acid, m.p. 182°–191°;

3-{N-[1-(2,6-dimethoxyphenyl)ethyl]amino}-2(S)-hydroxy-propyl-(benzyl)-phosphinic acid, m.p. 130°–162°;

3-{N-[1-(3,4-methylenedioxyphenyl)ethyl]amino}-2(S)-hydroxy-propyl-(benzyl)phosphinic acid, m.p. 200°–219°;

3-{N-[1-(3,4-dimethoxyphenyl)ethyl]amino}-2(S)-hydroxy-propyl-(benzyl)-phosphinic acid, m.p. 199°–208°, and 3-{N-[1-(2,4-dimethoxyphenyl)ethyl]amino}-2(S)-hydroxy-propyl-(benzyl)-phosphinic acid, m.p. 192°–202°.

EXAMPLE 13

In a manner analogous to that described in Example 6 it is possible to prepare

3-{N-[1-(2,5-dimethoxyphenyl)ethyl]amino}-2(S)-hydroxy-propyl-(cyclohexylmethyl)-phosphinic acid, m.p. 140°–149°;

3-{N-[1-(2,6-dimethoxyphenyl)ethyl]amino}-2(S)-hydroxy-propyl-(cyclohexylmethyl)-phosphinic acid, m.p. 172°–185°;

3-{N-[1-(3,4-dimethoxyphenyl)ethyl]amino}-2(S)-hydroxy-propyl-(cyclohexylmethyl)-phosphinic acid, m.p. 189°–195°;

3-{N-[1-(2,4-dimethoxyphenyl)ethyl]amino}-2(S)-hydroxy-propyl-(cyclohexylmethyl)-phosphinic acid, m.p. 156°–171°;

3-{N-[1-(3,4-methylenedioxyphenyl)ethyl]amino}-2(S)-hydroxy-propyl-(cyclohexylmethyl)-phosphinic acid, m.p. 190°–202°;

3-[N-(3,4-methylenedioxybenzyl)amino]-2(S)-hydroxy-propyl-(cyclohexylmethyl)-phosphinic acid, m.p. 176°–178°, and 3-{N-[1-(3,5-dimethoxyphenyl)ethyl]amino}-2(S)-hydroxy-propyl-(cyclohexylmethyl)-phosphinic acid, $^1$H-NMR (CD$_3$OD): δ=6.67 (3H, m), 6.53 (1H, m), 4.38–4.11 (2H, m), 3.85 (6H, s), 3.2–2.69 (2H, m), 2.10–1.58 (12H, m), 1.40–0.95 (4H, m).

EXAMPLE 14

20 mg of 5% palladium-on-carbon are added to a solution of 0.125 g of 3-{N-[1-(3,4-dichlorophenyl)ethyl]amino}-2(S)-hydroxy-propyl-(cyclohex-3-enylmethyl)-phosphinic acid in 5 ml of ethanol and hydrogenated at room temperature and normal pressure for 15 minutes. The catalyst is filtered off through Celite® and the filtrate is adjusted to pH 1 with ethanolic hydrochloric acid. Removal of the solvent and recrystallisation from isopropanol yield 3-{N-[1-(3,4-dichlorophenyl)ethyl]amino} -2(S)-hydroxy-propyl-(cyclohexylmethyl)-phosphinic acid, m.p. 173°–178°.

EXAMPLE 15

2.0 g of sodium cyanoborohydride are added in portions to a solution of 6.27 g of 3-aminopropyl-(cyclohexylmethyl)-phosphinic acid and 5.0 g of 3,5-dichlorobenzaldehyde and 1.91 g of glacial acetic acid in 50 ml of anhydrous methanol and the mixture is stirred at room temperature for 4 days. The solvent is removed, the white residue is taken up in 2.0M hydrochloric acid and filtered. The filtrate is concentrated to dryness by evaporation and the white solid that remains behind is suspended in ethyl acetate, filtered off and crystallised from propanol, yielding 3-[(3,5-dichlorobenzyl)amino]-propyl-(cyclohexylmethyl)-phosphinic acid, m.p. 231°–233°.

EXAMPLE 16

In a manner analogous to that described in Example 15 it is possible to prepare 3-[N-(quinolin-4-ylmethylamino)-propyl-(cyclohexylmethyl)-phosphinic acid, m.p. 175°–177° (decomposition).

EXAMPLE 17

In a manner analogous to that described in Example 15 it is possible to prepare 3-[N-(4-chlorobenzyl)-N-methylamino]-propyl-(cyclohexylmethyl)-phosphinic acid, m.p. 211°–213°.

EXAMPLE 18

In a manner analogous to that described in Example 15 it is possible to prepare 3-[N-(3,4-chlorobenzyl)amino]-propyl-(butyl)-phosphinic acid, m.p. 216°–217°.

EXAMPLE 19

In a manner analogous to that described in Example 15 it is possible to prepare 3-{N-[1-(4-chlorophenyl)ethylamino]}-propyl-(butyl)-phosphinic acid, m.p. 177°–179°.

EXAMPLE 20

In a manner analogous to that described in Example 15 it is possible to prepare 3-{N-[1-(3,4-dichlorophenyl)ethylamino]}-propyl-(butyl)-phosphinic acid, m.p. 134°–136°.

EXAMPLE 21

In a manner analogous to that described in Example 2 it is possible to prepare 3-{N-[1-(3-chloro-4-iodo-phenyl)ethyl]amino}-2(S)-hydroxy-propyl-(cyclohexylmethyl)-phosphinic acid, m.p. 120°–155°.

The starting material can be prepared as follows:

0.41 g of sodium cyanoborohydride is added to a solution of 1.86 g of 3-chloro4-iodo-acetophenone and 5.0 g of ammonium acetate in 25 ml of methanol and the mixture is stirred at room temperature for 20 hours. The reaction mixture is cooled to 4°, adjusted to pH 1 with hydrochloric acid and concentrated by evaporation under reduced pressure, and the residue is taken up in water and washed with ether. The aqueous phase is adjusted to pH 10 with potassium hydroxide and extracted with ether. The ether extract is dried over sodium sulfate and concentrated by evaporation. The free amine remaining behind in the form of an oil is dissolved in ether and adjusted to pH 1 with ethanolic hydrochloric acid. A white residue is formed which is filtered off and dried under reduced pressure, yielding 3-chloro-4-iodo-benzylammonium chloride having a melting point of 220°–222°.

EXAMPLE 22

In a manner analogous to that described in Example 21 it is possible to prepare 3-{N-[1-(4-chloro-3-iodo-phenyl)ethyl]amino}-2(S)-hydroxy-propyl-(cyclohexylmethyl)-phosphinic acid, m.p. 118°–124°.

EXAMPLE 23

In a manner analogous to that described in Example 6 it is possible to prepare 3-{N-[1-(4-chloro-3-iodo-phenyl)ethylamino]propyl-(diethoxymethyl)-phosphinic acid.

EXAMPLE 24

In a manner analogous to that described in Example 2 it is possible to prepare 3-{N-[1(S)-(3,4-dichlorophenyl)ethyl] amino}-2(S)-hydroxy-propyl-(cyclohexylmethyl)-phosphinic acid hydrochloride, m.p. 207.5°–209°.

EXAMPLE 25

In a manner analogous to that described in Example 2 it is possible to prepare 3-{N-[1(S)-(3,4-dichlorophenyl)ethyl] amino}-2(R)-hydroxy-propyl-(cyclohexylmethyl)-phosphinic acid hydrochloride; $^1$H-NMR (CD$_3$OD): δ=7.71 (1H), 7.63 (1H), 7.44 (1H), 4.45 (1H, q), 4.20 (1H), 3.02 (2H, CH$_2$N), 2.10–1.59 (12H, m), 1.39–0.95 (6H, m).

The starting material, 1(S)-(3,4-dichlorophenyl)ethylamine, can be prepared, for example, as follows:

A solution of 10.65 g of L-(+)-mandelic acid in 39 ml of ethanol at a temperature of 60° is added to a solution of 22.0 g of 1-(3,4-dichlorophenyl)ethylamine in 58 ml of ethanol at a temperature of 60°. The mixture is allowed to cool slowly to room temperature, and after 48 to 72 hours the solid portion is filtered off, washed with cold ethanol and dried under reduced pressure at 60°. Recrystallisation from ethanol yields the optically pure diastereoisomeric salt. Treatment thereof with sodium hydroxide and subsequent extraction with ether yields, after removal of the ether, (−)-[1(S)-(3,4-dichlorophenyl)ethyl]amine, $[α]_{20}^D$=−26.3°±1.0° (c=0.995 in methanol).

The mother liquors are concentrated to dryness by evaporation and the resulting residue is treated with aqueous sodium hydroxide solution and extracted with ether. The oil that remains behind (12 g) is treated as described above with 10.5 g of D-(−)-mandelic acid and yields, after recrystallisation and liberation of the amine, (+)[1(R)-(3,4-dichlorophenyl)ethyl]amine, $[α]_{20}^D$=+25°±1.0° (c=0.995 in methanol).

EXAMPLE 26

In a manner analogous to that described in Example 2 it is possible to prepare 3-{N-[1(R)-(3,4-dichlorophenyl)ethyl]amino}-2(R)-hydroxy-propyl-(cyclohexylmethyl)-phosphinic acid hydrochloride.

The starting material, 1(R)-(3,4-dichlorophenyl)ethylamine, can be prepared, for example, as follows:

The mother liquors from the racemate separation according to Example 21 are concentrated to dryness by evaporation and the resulting residue is treated with aqueous sodium hydroxide solution and extracted with ether. The oil that remains behind (12 g) is treated as described above with 10.5 g of D-(−)-mandelic acid and yields, after recrystallisation and liberation of the amine, (+)[1(R)-(3,4-dichlorophenyl)ethyl]amine, $[α]_{20}^D$=+25°±1.0° (c=0.995 in methanol).

EXAMPLE 27

In a manner analogous to that described in Example 2 it is possible to prepare 3-{N-[1(R)-(3,4-dichlorophenyl)ethyl]amino}-2(S)-hydroxy-propyl-(cyclohexylmethyl)-phosphinic acid hydrochloride, m.p. 184°–186°.

EXAMPLE 28

In a manner analogous to that described in Example 21 it is possible to prepare 3-{N-[1-(3-chloro-4-iodo-phenyl)ethyl]amino}-2(S)-hydroxy-propyl-(cyclohexylmethyl)-phosphinic acid hydrochloride; $^1$H-NMR (CD$_3$OD): δ=8.04 (1H, d), 7.71 (1H, d), 7.20 (1H, dd), 4.45 (1H, q), 4.23 (1H, m), 3.25–3.07 (1H, dd), 3.05–2.80 (1H, dd), 2.10–1.58 (12H, m), 1.56–0.99 (6H, d).

EXAMPLE 29

In a manner analogous to that described in Example 21 it is possible to prepare 3-{N-[1-(3-chloro-4-iodo-phenyl)ethyl]amino}-2(S)-hydroxy-propyl-(benzyl)-phosphinic acid hydrochloride, m.p. 198°–210°.

EXAMPLE 30

In a manner analogous to that described in Example 21 it is possible to prepare 3-{N-[1-(3-chloro-4-iodo-phenyl)ethyl]amino} propyl-(diethoxymethyl)-phosphinic acid and 3-{N-[1-(3-chloro-4-iodo-phenyl)ethyl]amino} propyl-(cyclohexylmethyl)-phosphinic acid, m.p. 184°–186°.

EXAMPLE 31

10 ml of water and 0.24 g of lithium hydroxide are added to a solution of 2.05 g of 3-{N-[1(S)-(3,4,5- trimethoxyphenyl)ethyl]amino}-2(S)-hydroxy-propyl-(benzyl)-phosphinic acid ethyl ester in 4 ml of water and the mixture is heated at reflux overnight. The then clear solution is cooled to room temperature, adjusted to pH 7 with phosphoric acid and concentrated to dryness by evaporation under reduced pressure. The evaporation residue is made into a slurry in hot methanol and filtered. After concentration of the filtrate by evaporation there remains a foam which, after crystallisation from isopropanol, yields 3-{N-[1(S)-(3,4,5 -trimethoxyphenyl)ethyl] amino}-2(S)-hydroxy-propyl-(benzyl)-phosphinic acid having a melting point of 204°–206°, $[\alpha]_{20}^D=-35.2°\pm1.2°$ (c=0.812 in methanol).

The starting material can be prepared, for example, as follows:

Crystallisation of the mandelic acid salt of 1-(3,4,5-trimethoxyphenyl)ethylamine from ethanol and liberation of the free base yield enantiomerically pure 1(S)-(3,4,5-trimethoxyphenyl)ethylamine which can be reacted with 3-chloro-2(R)-hydroxy-propyl-(benzyl)-phosphinic acid ethyl ester in a manner analogous to that described in Example 2.

EXAMPLE 32

0.254 g of lithium hydroxide and 6 ml of water are added to a solution of 2.26 g of 3-[N-(3,4-dichlorobenzyl)amino] -2(S)-hydroxy-propyl(diethoxymethyl)phosphinic acid ethyl ester in 3 ml of ethanol and the mixture is stirred at 60° for 24 hours. The mixture is allowed to cool to room temperature, adjusted to pH 7 with aqueous phosphoric acid and concentrated to dryness by evaporation. The evaporation residue is made into a slurry in hot methanol and filtered. The filtrate is concentrated to dryness by evaporation and the glassy evaporation residue is taken up in a small amount of ethanol. The pH value is adjusted to pH 1 with ethanolic hydrochloric acid and the solvent is removed. Crystallisation from acetonitrile yields 3-[N-(3,4-dichlorobenzyl)amino] -2(S)-hydroxy-propyl(diethoxymethyl)phosphinic acid; $[\alpha]_{20}^D=-10.8°\pm1.7°$ (c=0.595 in methanol); $^1$H-NMR (CD$_3$OD): δ=7.76 (1H, m), 7.61 (1H, m), 7.45 (1H, m), 4.47 (1H, d), 4.29 (1H, m), 4.20 (2H, m), 3.80 (2H, m), 3.69 (2H, m), 3.25 (1H, dd), 3.02 (1H, d, d), 2.04 (1H, dd), 1.87 (1H, d, d); 1.20 (6H, t).

The starting material can be prepared, for example, as follows:

With stirring under an argon atmosphere, 133 ml of trimethylchlorosilane are added dropwise to a solution of 227 g of diethoxymethylphosphinic acid ethyl ester in 1500 ml of diethyl ether and 145 ml of triethylamine (1 hour). The reaction is slightly exothermic and a white precipitate is formed. The reaction mixture is stirred at room temperature for 20 hours, filtered under argon and concentrated to dryness by evaporation. 63 g of (R)-epichlorohydrin are added to the oil that remains behind. When the exothermic reaction has died away, the mixture is heated at 70° for 24 hours, then allowed to cool to room temperature, diluted with dichloromethane and washed with water. The organic phase is separated off, dried over sodium sulfate and concentrated by evaporation. The evaporation residue is taken up in 220 ml of 1% methanolic acetic acid, stirred at room temperature for 24 hours and again concentrated to dryness by evaporation. The evaporation residue is purified by chromatography on silica gel and yields 3-chloro-2(R)-hydroxy-propyl-(diethoxymethyl)phosphinic acid ethyl ester in the form of a colourless oil; $[\alpha]_{20}^D=-16.0°\pm1.2°$ (c=0.86 in chloroform); $^1$H-NMR (CD$_3$Cl$_3$): δ=4.70 (1Hd, CHP), 4.34 (1H, m, CHO), 4.20 (1H, m, CH$_2$OP), 3.87 (2H, m, CH$_2$OC), 3.60 (2H, d, CH$_2$Cl), 2.31–1.96 (2H, m, CH$_2$P), 1.35 (3H, t, CH$_3$), 1.28 (6H, t, 2xCH$_3$).

A solution of 7.2 g of 3-chloro-2(R)-hydroxy-propyl-(diethoxymethyl)phosphinic acid ethyl ester, 3.6 g of Hünig base and 6.5 g of 3,4-dichlorobenzylamine in 20 ml of anhydrous ethanol is heated at reflux for 4 days. The mixture is concentrated to dryness by evaporation and the residue is partitioned between dichloromethane and water. The organic phase is separated off, dried over sodium sulfate, concentrated by evaporation and purified by chromatography on silica gel, yielding 3-[N-(3,4-dichlorobenzyl)amino] -2(S)-hydroxy-propyl(diethoxymethyl)phosphinic acid ethyl ester in the form of a yellowish oil; $^1$H-NMR (CD$_3$Cl$_3$/D$_2$O): δ=7.43 (1H, m, phenyl), 7.39 (1H, m, phenyl), 7.15 (1H, m, phenyl), 4.70 (1H, s, CHP), 4.20 (3H, m, CHO+CH$_2$OP), 3.83 (2H, m, CH$_2$OC), 3.70 (4H, m, CH$_2$phenyl+CH$_2$OC), 2.65 (2H, m, CH$_2$N), 2.20–1.71 (2H, m, CH$_2$P), 1.40–1.26 (6H, m, 3xCH$_3$).

EXAMPLE 33

In a manner analogous to that described in Example 2 it is possible to prepare 3-{N-[1-(4-chloro-3-iodo-phenyl)ethyl]amino}-2(S)-hydroxy-propyl(diethoxymethyl)phosphinic acid; $^1$H-NMR (CD$_3$OD): δ=8.10 (1H, d), 7.58 (2H, m), 4.45–4.18 (3H, m), 3.85 (4H, m), 2.98 (2H, AB$_2$, d), 2.10–1.52 (5H, m).

EXAMPLE 34

In a manner analogous to that described in Examples 1 to 5, 6, 7 and 12 to 29 it is also possible to prepare the compounds listed below:

3-{N-[1(R)-(3,4-dichlorophenyl)ethyl]amino}-2(S)-hydroxy-propyl-(cyclohex-3-enylmethyl)-phosphinic acid, 3-{N-[1(S)-(3,4-dichlorophenyl)ethyl]amino}-2(S)-hydroxy-propyl-(cyclohex-3-enylmethyl)-phosphinic acid, 3-{N-[1(R)-(3,4-dichlorophenyl)ethyl]amino}-2(R)-hydroxy-propyl-(cyclohex-3-enylmethyl)-phosphinic acid, 3-{N-[1(S)-(3,4-dichlorophenyl)ethyl]amino}-2(S)-hydroxy-propyl-(benzyl)-phosphinic acid, 3-{N-[1(S)-(3,4-dichlorophenyl)ethyl]amino}-2(S)-hydroxy-propyl-(diethoxymethyl)-phosphinic acid, 3-{N-[1(R)-(3,4-dichlorophenyl)ethyl]amino}-2(S)-hydroxy-propyl-(diethoxymethyl)-phosphinic acid, 3-{N-[3-(3,4-dichlorophenyl)propyl]amino}-2(S)-hydroxy-propyl-(benzyl)-phosphinic acid, 3-{N-[3(R)-(phenyl)prop-2(R)-yl]amino}-2(S)-hydroxy-propyl-(benzyl)-phosphinic acid, 3-{N-[3(R)-(phenyl)prop-2(R)-yl]amino}-2(S)-hydroxy-propyl-(cyclohexylmethyl)-phosphinic acid, 3-{N-[3(R)-(phenyl)-3-hydroxy-prop-2(R)-yl]amino}-2(S)-hydroxy-propyl-(benzyl)-phosphinic acid, 3-{N-[3(R)-(phenyl)-3-hydroxy-prop-2(R)-yl]amino}-2(S)-hydroxy-propyl-(cyclohexylmethyl)-phosphinic acid, 3-{N-[3-(3,4-dichlorophenyl)-3-hydroxy-prop-2-yl]amino}-2(S)-hydroxy-propyl-(benzyl)-phosphinic acid, 3-{N-[2-(3,4-dichlorophenyl)propyl]amino}-2(S)-hydroxy-propyl-(cyclohexylmethyl)-phosphinic acid, 3-{N-[2-(3,4-dichlorophenyl)propyl]amino}-2(S)-hydroxy-propyl-(benzyl)-phosphinic acid, 3-{N-[3-(3,4-dichlorophenyl)prop-2- yl]amino}-2(S)-hydroxy-propyl-(benzyl)-phosphinic acid, 3-{N-[4-(3,4-dichlorophenyl)but-3-yl]amino}-2(S)-hydroxy-propyl-(benzyl)-phosphinic acid, 3-{N-[1-(3,4-dichlorophenyl)-2-hydroxy-ethyl]amino}-2(S)-hydroxy-propyl-(benzyl)-phosphinic acid, 3-{N-[2-(3,4-dichlorophenyl)-2-hydroxy-ethyl]amino}-2(S)-hydroxy-propyl-(benzyl)-phosphinic acid, 3-{N-[1(S)-(3-chlorophenyl)ethyl]amino} propyl-(cyclohexylmethyl)-phosphinic acid, and 3-{N-[1(S)-(3-chlorophenyl)ethyl]amino}-2(S)-hydroxy-propyl-(cyclohexylmethyl)-phosphinic acid.

EXAMPLE 35

0.2 g of lithium hydroxide and 4 ml of water are added to a solution of 1.1 g of 3-amino-2(S)-hydroxy-propyl-(cyclohex-3-enyl)-phosphinic acid ethyl ester in 4 ml of ethanol. The mixture is heated to 60° and stirred for 20 hours. The mixture is then allowed to cool to room temperature, adjusted to pH 7 with aqueous phosphoric acid, concentrated to dryness by evaporation, taken up in methanol/water and filtered. After removal of the solvent there remains behind a foam which, after crystallisation from ethanol/methanol, yields 3-amino-2(S)-hydroxy-propyl-(cyclohex-3-enyl)-phosphinic acid in the form of white crystals having a melting point of 221°–225°.

The starting material can be prepared, for example, as follows:

Under nitrogen, 8.7 g of sodium hydride (99%) dissolved in 600 ml of tetrahydrofuran are cooled to 15° and 75 g of 1,1-diethoxyethylphosphinic acid ethyl ester in 100 ml of tetrahydrofuran are added thereto in the course of 1 hour, the reaction temperature being maintained at less than 25°. The resulting suspension is stirred at room temperature for 2 hours and then a solution of 57.2 g of bromomethylcyclohex-3-ene in 100 ml of anhydrous tetrahydrofuran is added thereto in the course of 30 minutes. The mixture is heated at reflux for 24 hours, then cooled to 0°; 10 ml of water are added and the solvent is removed. The residue is dissolved in dichloromethane, washed twice with water, dried over sodium sulfate, concentrated to dryness by evaporation and distilled. The resulting 1,1-diethoxyethyl-(cyclohex-3-ene)-phosphinic acid ethyl ester is dissolved in 300 ml of dichloromethane that contains 10% by volume ethanol and left to stand at room temperature for 24 hours. Removal of the solvent and distillation yield cyclohex-3-enylmethylphosphinic acid ethyl ester;, $^{31}$P-NMR (CDCl$_3$): δ=37.1 (s).

10.6 g of trimethylchlorosilane are added to a solution of 16.8 g of cyclohex-3-enylmethylphosphinic acid ethyl ester and 9.9 g of triethylamine in 120 ml of tetrahydrofuran and the mixture is stirred at room temperature for 24 hours. The mixture is then filtered under argon and concentrated to dryness by evaporation. 9.1 g of (R)-epichlorohydrin and 1.1 g of anhydrous zinc chloride are added to the oil that remains behind. An exothermic reaction begins and after the reaction has died away the mixture is stirred at 80° for 16 hours. The reaction mixture is cooled to room temperature, diluted with dichloromethane and washed with water. The organic phase is separated off, dried over sodium sulfate and concentrated to dryness by evaporation. The colourless oil that remains behind is dissolved in 250 ml of methanol that contains 1% by volume glacial acetic acid and is left to stand at room temperature for 24 hours. Removal of the solvent and chromatography of the residue on silica gel yield 3-chloro-2(S)-hydroxy-propyl-(cyclohex-3-enyl)-phosphinic acid ethyl ester, $[\alpha]_{20}^D$=+10.0±1.2 (c=0.84 in trichloromethane).

A solution of 2.0 g of 3-chloro-2(S)-hydroxy-propyl-(cyclohex-3-enyl)-phosphinic acid ethyl ester in 40 ml of ethanol is placed in an autoclave. 10.0 g of ammonia are introduced under pressure and the mixture is left to stand at room temperature for 72 hours, concentrated to dryness by evaporation, chromatographed on silica gel, stirred at 0° with ethyl acetate/diethyl ether and filtered with suction, yielding 3-amino-2(S)-hydroxy-propyl-(cyclohex-3-enyl)-phosphinic acid ethyl ester, $[\alpha]_{20}^D$=−5.2±0.9 (c=1.07 in methanol).

EXAMPLE 36

In a manner analogous to that described in Example 35 it is possible to prepare 3-amino-2(S)-hydroxy-propyl-(4-chlorbenzyl)-phosphinic acid hydrochloride, m.p. 158°–162°.

EXAMPLE 37

In a manner analogous to that described in Example 35 it is possible to prepare 3-amino-2(S)-hydroxy-propyl-(4-methylbenzyl)-phosphinic acid hydrochloride, m.p. 174°–176°.

EXAMPLE 38

In a manner analogous to that described in Example 35 it is possible to prepare 3-amino-2(S)-hydroxy-propyl-(4-methoxybenzyl)-phosphinic acid.

EXAMPLE 39

Tablets each comprising 200 mg of 3-{N-1-(3,4-Dichlorphenyl)-ethyl]amino} -2(S)-hydroxy-propyl(cyclohexylmethyl)phosphinic acid or a salt, for example the hydrochloride, thereof can be prepared as follows:

| Composition (10000 tablets) | |
| --- | --- |
| active ingredient | 2000.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch, and the mixture is moistened with an ethanolic solution of the gelatin and granulated through a sieve. After drying, the remainder of the potato starch, the magnesium stearate, the talc and the silicon dioxide are mixed in and the mixture is compressed to form tablets each weighing 295.0 mg and comprising 200.0 mg of active ingredient; if desired the tablets may be provided with dividing notches for finer adaptation of the dose.

EXAMPLE 40

Film-coated tablets each comprising 400 mg of 3-{N-1-(3,4-Dichlorphenyl)ethyl]amino} -2(S)-hydroxy-propyl(cyclohexylmethyl)phosphinic acid or a salt, for example the hydrochloride, thereof can be prepared as follows:

| Composition (for 1000 film-coated tablets) | |
| --- | --- |
| active ingredient | 400.0 g |
| lactose | 100.0 g |
| corn starch | 70.0 g |
| talc | 8.5 g |
| calcium stearate | 1.5 g |
| hydroxypropylmethylcellulose | 2.36 g |

| Composition (for 1000 film-coated tablets) | |
|---|---|
| shellac | 0.64 g |
| water | q.s. |
| methylene chloride | q.s. |

The active ingredient, the lactose and 40 g of the corn starch are mixed together and moistened with a paste prepared from 15 g of corn starch and water (with heating), and granulated. The granules are dried and the remainder of the corn starch, the talc and the calcium stearate are added and mixed with the granules. The mixture is compressed to form tablets (mg) which are then film-coated with a solution of the hydroxypropylmethylcellulose and the shellac in methylene chloride; final weight of the film-coated tablet: 580 mg.

EXAMPLE 41

Hard gelatin capsules comprising 500 mg of active ingredient, for example 3-{N- 1-(3,4-Dichlorphenyl)ethyl]amino}-2(S)-hydroxy-propyl(cyclohexylmethyl)-phosphinic acid or a salt, for example the hydrochloride, thereof can be prepared, for example, as follows:

| Composition (for 1000 capsules) | |
|---|---|
| active ingredient | 500.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added through a sieve of 0.2 mm mesh size to the lyophilised active ingredient. The two components are intimately mixed. Then first the lactose is added through a sieve of 0.6 mm mesh width and then the microcrystalline cellulose is added through a sieve of 0.9 mm mesh width. The mixture is then again intimately mixed for 10 minutes. Finally, the magnesium stearate is added through a sieve of 0.8 mm mesh width. After stirring for a further 3 minutes, 790 mg portions of the resulting formulation are introduced into hard gelatin capsules of suitable size.

EXAMPLE 42

A 5% injection or infusion solution of 3-{N-1-(3,4-Dichlorphenyl)ethyl]amino} -2(S)-hydroxy-propyl(cyclohexylmethyl)phosphinic acid or a salt, for example the hydrochloride, thereof, can be prepared, for example, as follows:

| Composition (for 1000 or 400 ampoules) | |
|---|---|
| active ingredient | 125.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a microfilter. The buffer solution is added and the mixture is made up to 2500 ml with water. For the preparation of unit dose forms, 1.0 ml or 2.5 ml portions are introduced into glass ampoules which then comprise 50 mg or 125 mg of active ingredient, respectively.

What is claimed is:

1. A compound of formula I

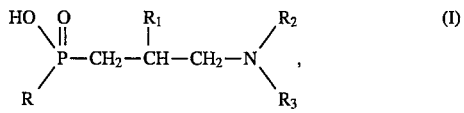

wherein

R is cyclohexylmethyl, $R_1$ is hydroxy and $R_2$ is 3,4-methylenedioxybenzyl, or 1-(3,4-methylenedioxyphenyl)ethyl, and $R_3$ is hydrogen, or R is benzyl, $R_1$ is hydroxy, $R_2$ is 1-(3,4-methylenedioxyphenyl) ethyl, and $R_3$ is hydrogen, or a salt thereof.

2. A compound according to claim 1 of formula I wherein R is cyclohexylmethyl or benzyl, $R_1$ is hydroxy, $R_2$ is 1-(3,4-methylenedioxyphenyl)ethyl, and $R_3$ is hydrogen, or a salt thereof.

3. A compound according to claim 1 wherein $R_1$ is hydroxy and the carbon atom carrying the hydroxy group and, where present, the α-carbon atom of 3,4-methylenedioxy-phenyl)ethyl has the (S)-configuration, R, $R_2$ and $R_3$ being as defined in each case.

4. A compound according to claim 1 being 3-{N-[1-(3,4-Methylenedioxyphenyl)ethyl]amino} -2(S)-hydroxy-propyl-(benzyl)-phosphinic acid or a salt thereof.

5. A compound according to claim 1 being 3- [N-[1-(3,4-Methylenedioxyphenyl)ethyl]amino} -2(S)-hydroxy-propyl-(cyclohexylmethyl)-phosphinic acid or a salt thereof.

6. A compound according to claim 1 being 3-[N-(3,4-Methylenedioxybenzyl)amino] -2(S)-hydroxy-propyl-(cyclohexylmethyl)-phosphinic acid or a salt thereof.

7. A compound according to claim 1 being

3-{N-[1-(3,4Methylenedioxyphenyl)ethyl]amino}-2(S)-hydroxy-propyl-(benzyl)phosphinic acid;

3-{N-[1-(3,4-Methylenedioxyphenyl)ethylamino}-2(S)-hydroxy-propyl(cyclohexylmethyl)-phosphinic acid;

3-[N-(3,4Methylenedioxybenzyl)amino]-2(S)-hydroxy-propyl-(cyclohexylmethyl)phosphinic acid;

or a salt thereof.

8. A pharmaceutical composition for the treatment of epilepsy comprising art effective amount of a compound according to claim 1 together with a customary pharmaceutical carrier.

9. A method of treatment of symptoms of epilepsy comprising administering a therapeutically effective amount of a compound according to claim 1 or a pharmaceutically acceptable salt thereof to a warm-blooded organism in need of such treatment.

* * * * *